US00PP22208P3

(12) United States Plant Patent

Bliss et al.

(10) Patent No.: US PP22,208 P3

(45) Date of Patent: Oct. 25, 2011

(54) PEACH ROOTSTOCK NAMED 'HBOK 50'

(50) Latin Name: *Prunus persica*
Varietal Denomination: 'HBOK 50'

(75) Inventors: Fredrick A. Bliss, Davis, CA (US); Ali A. Almehdi, Davis, CA (US); Theodore M. DeJong, Davis, CA (US); Anne Gillen, Leland, MS (US); Craig A. Ledbetter, Clovis, CA (US)

(73) Assignees: The Regents of the University of California, Oakland, CA (US); The United States of America, as represented by the Secretary of Agriculture, Washington, DC (US)

( * ) Notice: Subject to any disclaimer, the term of this patent is extended or adjusted under 35 U.S.C. 154(b) by 48 days.

(21) Appl. No.: 12/653,858

(22) Filed: Dec. 17, 2009

(65) Prior Publication Data

US 2011/0154547 P1 Jun. 23, 2011

(51) Int. Cl.
*A01H 5/00* (2006.01)

(52) U.S. Cl. ..... Plt./180

(58) Field of Classification Search ..... Plt./180, Plt./194

See application file for complete search history.

(56) References Cited

PUBLICATIONS

The Apr. 1, 2008 Test Agreement For Trees/Rootstocks (No. 2008-5019) between Duarte Nursery, Inc. and The Regents Of The University of California, 7 pages.

The Apr. 1, 2008 Test Agreement For Trees/Rootstocks (No. 2008-5012) between Paramount Farming Company and The Regents Of The University of California, 7 pages.

The Jan. 1, 2003 Test Agreement For Rootstocks (No. 2003-5021) between Jim Krause/Redwood Orchards and The Regents Of The University of California, 6 pages.

The Jan. 1, 2008 Test Agreement For Trees/Rootstocks (No. 2008-5016) between Fowler Nurseries, Inc. and The Regents Of The University of California, 8 pages.

The Jan. 15, 2003 Test Agreement For Trees (No. 2004-5016) between Jim Krause/Redwood Orchards and The Regents Of The University of California, 8 pages.

The Mar. 1, 2009 Test Agreement For Trees/Rootstocks (No. 2009-5012) between Burchell Nursery, Inc. and The Regents Of The University of California, 7 pages.

*Primary Examiner* — Susan McCormick Ewoldt

(74) *Attorney, Agent, or Firm* — Morrison & Foerster LLP

(57) ABSTRACT

A new and distinct variety of peach rootstock denominated 'HBOK 50' is described. The 'HBOK 50' peach rootstock offers size control ability, root knot nematode resistance, less wood from dormant and summer pruning, and production of fewer root suckers. 'HBOK 50' has contributed to size reduction of compound trees when it is used as a clonally-produced rootstock with the fresh market peach "O'Henry". No evidence of graft incompatibility or other abnormalities have been noted in such circumstances. Fruit on compound trees with 'HBOK 50' rootstocks is either similar in size or smaller than 'Nemaguard'. The 'HBOK 50' rootstock displays root knot nematode resistance levels similar to 'Nemaguard' and more resistant than 'Lovell'.

7 Drawing Sheets

STATEMENT REGARDING FEDERALLY SPONSORED RESEARCH OR DEVELOPMENT

This invention was made with Government support under Grant No. USDA NRICGP 95-37300-1585, awarded by the United States Department of Agriculture National Initiative for Competitive Grants Program, Project 5967-CG. The Government may have certain rights in this invention.

Latin name: Botanical/commercial classification: *Prunus persica* 'L. Batsch new clonal peach rootstock.

Varietal denomination: The varietal denomination of the claimed peach rootstock is 'HBOK 50'.

BACKGROUND OF THE INVENTION

The present invention relates to a new and distinct cultivar of peach rootstock (*Prunus persica*) that has been denominated as 'HBOK 50' and more particularly to a peach rootstock that is graft compatible with peach and nectarine scion cultivars, and confers moderate vigor control on compound trees, produce fewer root suckers than 'Nemaguard', and is resistant to the rootknot nematode *Meloidogyne incognita* (race 1) isolate 'Beltran'.

It is recognized that vigor control of compound trees on a standard rootstock, such as 'Nemaguard', is difficult to achieve and to do so requires extensive pruning both in mid summer and the dormant season. It is also recognized that root suckers produced on standard rootstock are required to be removed manually, resulting in cost to the grower. The 'HBOK 50' peach rootstock has modest vigor control that produces smaller trees, which requires less pruning, and much fewer root suckers than 'Nemaguard', which results in cost savings for the grower.

The peach rootstock of the present invention was created at Davis, Calif. In 1990 hybrid 'P248-139' was created by crossing 'Harrow Blood' (HB) with 'Okinawa' (OK) at Fresno Calif. 'Harrow Blood' was used as the female parent and 'Okinawa' was used as the male parent in the cross. Seeds resulting from the open pollination of a single $F_1$ plant from hybrid 'P248-139' were used to generate an experimental population (referred to as 'OP-$F_2$ population') in February of 1994. Fifty seven 'OP-$F_2$' seedlings were budded with 'O'Henry' (referred to as 'O'Henry population'), and concurrently each of these seedlings was budded onto 'Nemared' rootstock (referred to as 'OP-$F_2$ population'). There were no obvious defects in the bud unions indicating compatibility of scions and rootstocks at this stage. Compound trees of 'O'Henry' scion budded onto each seedling of the 'OP-$F_2$' segregating population as a rootstock were evaluated for trunk cross-sectional area (TCA), tree height, crop yield, cropping efficiency, fruit weight, and number of suckers. Eight seedlings were selected for further study of rootstock potential under semi-commercial conditions at Parlier, Calif. The primary criterion used for choosing seedlings having potential for size control as a rootstock was TCA. Wood from mother trees was propagated asexually (rooted), budded with 'O'Henry' peach scion and planted in a replicated field trial at Parlier, Calif. in 1999. 'HBOK' 50 was identified as a result of that trial, and was subsequently selected for further horticultural evaluation.

The new 'HBOK 50' peach rootstock of the present invention has been asexually reproduced by leaf cuttings at Davis, Calif. The distinctive characteristics of the new peach rootstock have been found to be stable and are transmitted to the new rootstocks when asexually propagated.

SUMMARY OF THE INVENTION

The 'HBOK 50' peach rootstock of the present invention has a peach pedigree (vs. inter-specific heritage) and offers size control ability, root knot nematode resistance, less wood from dormant and summer pruning, and production of fewer root suckers. When used as clonally-produced rootstocks with fresh market peach ('O' Henry' and 'Springcrest'), cling peach ('Ross'), and nectarine ('Mayfire' and 'Summer Fire') scions, they have contributed to size reduction of compound trees and no evidence of graft incompatibility or other abnormalities have been noted. Based on reduced tree height and smaller trunk cross-sectional area (TCA) compared to standard rootstocks, 'HBOK 50' had about a 7-8% size reduction. Although crop yield per tree usually was less than on 'Nemaguard' rootstock, the compound trees with 'HBOK 50' rootstocks that were smaller generally showed greater cropping efficiency. Ability to plant smaller trees at greater density in commercial fields provides an opportunity to recover economically viable yields per unit area. Fruit on compound trees with 'HBOK 50' rootstocks was either similar in size or smaller than 'Nemaguard'. The 'HBOK 50' rootstock displays root knot nematode resistance levels similar to 'Nemaguard' and more resistance than 'Lovell'. Compound plants with 'HBOK 50' rootstocks provide an opportunity for growers to develop new management practices that utilize the potential of these rootstocks to lower costs through size reduction, reduced pruning and less need for sucker control.

DETAILED DESCRIPTION OF THE INVENTION

Figure 1:
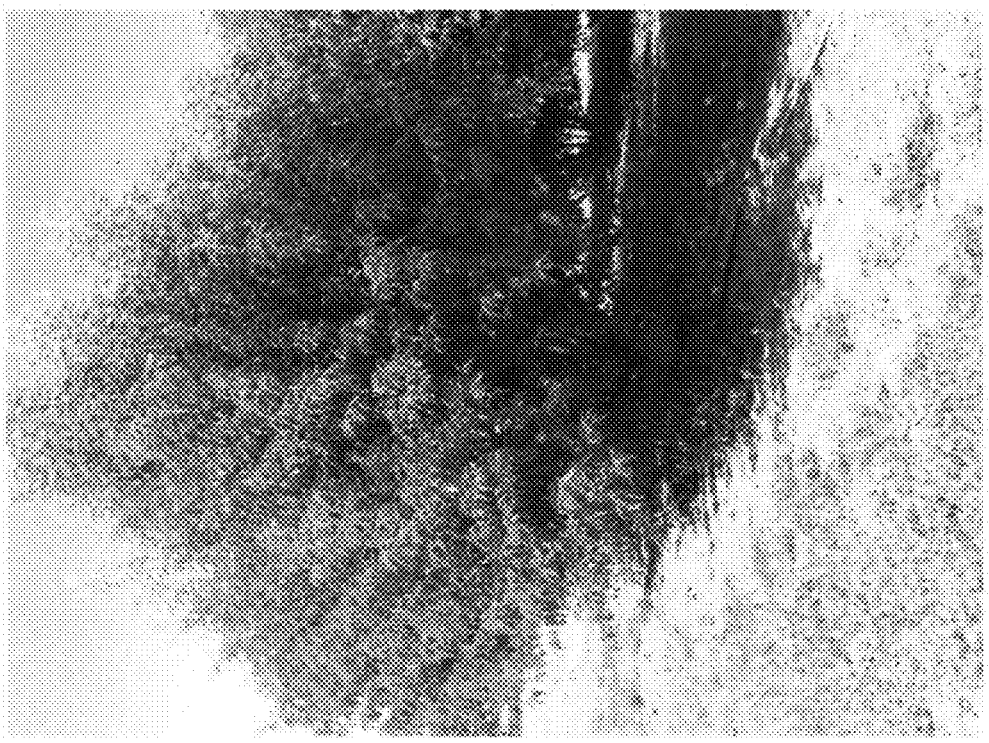
FIG. 1 shows a severely cut back tree of 'HBOK 50' with an abundance of vigorous, strait vegetative shoots, providing a large quantity of propagation materials for stem cuttings.

The peach rootstocks 'HBOK 10', 'HBOK 32' and 'HBOK 50' were developed to be improved rootstocks with size control capability and pest resistance. These three peach rootstocks were developed by:1) screening *Prunus* populations for compatibility with and growth controlling potential for peach and nectarine along with resistance to nematodes, crown gall and bacterial canker, 2) hybridizing parents with these traits and beginning selection in segregating populations for individuals that possess desired trait combinations, 3) identifying individual plants that are useful as asexually propagated clonal rootstocks, and 4) assessing the potential of the best materials for commercial peach and nectarine rootstocks.

'Okinawa' peach was identified as a parent for its resistance to the nematodes *M. incognita* and *M. javanica*. Additionally it has a low chill requirement resulting in early blooming and presumably early seed germination. It is not known to be size controlling and it is an open, standard-type tree on its own root. 'Harrow Blood' peach, selected in Canada as a rootstock, was chosen as a second parent because it was reported to have dwarfing effect on scions in early years of tree growth. It is susceptible to root-knot nematode, has a high chill requirement (late bloom), produces fruit with red flesh and is a small, 'twiggy' tree. The cross of 'Harrow Blood' and 'Okinawa' was previously performed in 1990 at Fresno, Calif. (USDA-ARS), and an $F_1$ hybrid of that cross was used.

An experimental population (referred to as 'OP-$F_2$ population') derived from open pollination in 1994, of a single $F_1$ plant (No. P248-139) of the cross 'Harrow Blood' (HB)× 'Okinawa' (OK) was generated and used.

Detailed research findings leading to the selection of the mother plants of the three rootstocks are presented in Gillen (2001). Briefly, 57 'OP-$F_2$' seedlings were budded with 'O'Henry' (referred to as 'O'Henry population') and concurrently each of these seedlings was budded onto 'Nemared' rootstock (referred to as 'OP-$F_2$ population') in 1995 and planted in spring 1996. Successful bud unions of 49 seedling pairs (98 paired plants) were produced for which tree characters were measured during 1997, 1998, and 1999. There were no obvious defects in the bud unions indicating compatibility of scions and rootstocks at this stage.

A commercial nursery prepared the 'OP-$F_2$ population' by field budding a scion of each $F_2$ plant onto 'Nemared' seedlings. The 'O'Henry population' was prepared at Davis, Calif., by budding 'O'Henry' onto each of the segregating seedlings which were grown in pots until transplanted to the field. After transplanting, the main stems of all plants were pruned to approximately 24 inches and primary lateral branches to about 18 inches. Although the two populations, 'OP-$F_2$' and 'O'Henry' were handled differently at the outset, trees within each population received uniform treatment to facilitate detection of genetic differences.

Root Knot Nematode Resistance Screen

The root knot nematode resistance response of each 'OP-$F_2$' seedling in the segregating population was determined from a progeny test in which open-pollinated ($F_3$) seedlings from each 'OP-$F_2$' plant were inoculated with live root-knot nematodes and scored for their reaction. Based on whether the 'OP-$F_3$' family was all resistant, all susceptible, or segregating, the 'OP-$F_2$' plant was considered to be homozygous resistant, homozygous susceptible or heterozygous, respectively assuming reaction to be controlled by a single gene. Preparation and application of inoculum and procedures for growing and scoring the plants and details of the screening procedure are presented in Gillen (2001). Based on the response phenotypes of the OP-$F_3$ families, the 'OP-$F_2$ population' segregated 9 homozygous resistant, 26 heterozygous, 12 homozygous susceptible, and two plants were unable to be scored. This segregation pattern was consistent with control by a single dominant gene (Chi Squared Goodness-of-fit Test; df=46, p=0.63). The seedlings 94-94-10 and 94-94-50 were scored as heterozygous resistant and 94-94-32 homozygous resistant for root knot nematode reaction (Gillen, 2001).

Seedling Selection for Size Control Potential

Compound trees consisting of 'O'Henry' scion budded onto each seedling of the 'OP-$F_2$' segregating population as a rootstock were planted at Davis, Calif. In 1997, 1998, and 1999, trees were evaluated for trunk cross-sectional area (TCA), tree height, crop yield, cropping efficiency, fruit weight and number of suckers. The size control phenotypes (TCA and tree height) of the seedlings in the segregating population showed a continuous distribution (measured as percentage of mean TCA of the standard) and no discrete segregation pattern was seen in this population.

Eight seedlings were selected based on the trials at Davis, Calif., for further study of rootstock potential under semi-commercial conditions at Parlier, Calif. The primary criterion used for choosing seedlings having potential for size control as a rootstock was TCA, since that is considered to be a better measure of bearing surface of a tree than height (Westwood, 1978). Wood from mother trees was propagated asexually (rooted), budded with 'O'Henry' peach scion and planted in a replicated field trial at the KAC in 1999, details of which are discussed in Gillen (2001). A total of 20 trees of each rootstock/scion combination were planted and trained to the perpendicular V system. Between-row spacing of 5.49 m (18 ft) was the same for all rootstock/scion combinations, and in-row spacing was 2.13 m (7 ft) between trees for all treatments. Four replications of 5 trees each were arranged according to a randomized complete block design. Data collected for plant height and TCA in 1999 showed that among the 8 entries, 94-94-10 ('HBOK 10'), 94-94-32 ('HBOK 32'), and 94-94-50 ('HBOK 50') were significantly smaller than the control in both 1999 and 2000 (Gillen, 2001). Data collection on 94-94-7 and 94-94-44 was discontinued after 1999. After 2000, testing was discontinued on 94-94-5 and 94-94-48, since they appeared to be the least promising (Table 1). During the four years of this trial tree height and TCA of the three experimental stocks were less than that of the controls (mean values of 'Nemaguard' and 'Lovell'). At the 2003 harvest year ($5^{th}$ leaf), 94-94-32 showed the most potential for size control followed by 94-94-10 and 94-94-50. 94-94-32 and 94-94-10 were significantly smaller than the control for all years (Table 1). Though 94-94-50 was smaller than the controls in all years it was not significantly so in 2003. In general, fruit weight was not different among trees with experimental rootstocks and the controls. Yield was consistently lower on the experimental rootstocks than the controls, though not always significantly less (Table 1). Pruning weights and suckering were less for the experimental rootstocks.

Table 1 below shows mean values for tree height, trunk cross sectional area (TCA), crop yield, fruit weight, cropping efficiency, winter pruning weight, and summer pruning weight of second-leaf through fifth-leaf 'O'Henry' peach scions on five 'HBOK' rootstocks and the control and mean number of root suckers on each of the rootstocks. Trees were planted at Parlier, Calif., in 1999.

TABLE 1

| Harvest year: 2000 (2nd leaf) | | | | | | |
|---|---|---|---|---|---|---|
| | Tree height (cm)* | | TCA (cm2)* | | Crop yield (kg/tree)* | |
| Rootstock | Mean* | S.E.M. | Mean | S.E.M. | Mean | S.E.M. |
| 94-94-5** | 303.0 ab | 10.08 | 33.6 ab | 3.41 | 1.3 bc | 0.18 |
| 94-94-10** | 237.0 c | 19.18 | 16.4 c | 2.95 | 0.5 c | 0.11 |
| 94-94-32** | 216.0 c | 15.33 | 13.5 c | 2.32 | 0.5 bc | 0.07 |
| 94-94-48** | 300.0 ab | 21.60 | 29.1 ab | 5.18 | 1.9 b | 0.37 |
| 94-94-50** | 260.0 bc | 10.73 | 23.8 bc | 2.28 | 0.7 bc | 0.14 |
| Control*** | 326.0 a | 12.41 | 35.4 a | 3.63 | 5.7 a | 0.61 |

| Harvest year: 2000 (2nd leaf) | | | | | | |
|---|---|---|---|---|---|---|
| | Fruit weight (g/fruit) | | Cropping efficiency (Crop | | Winter pruning weight | |
| Rootstock | Mean | S.E.M. | Mean | S.E.M. | Mean | S.E.M. |
| 94-94-5** | 179 a | 6.05 | 0.03 a | 0.01 | 5.2 a | 0.72 |
| 94-94-10** | 158 ab | 11.10 | 0.03 a | 0.01 | 1.8 cd | 0.66 |
| 94-94-32** | 134 b | 5.42 | 0.40 a | 0.01 | 1.2 d | 0.31 |
| 94-94-48** | 180 a | 24.45 | 0.07 a | 0.02 | 3.8 abc | 1.23 |
| 94-94-50** | 147 ab | 14.00 | 0.95 a | 0.01 | 2.2 bcd | 0.55 |
| Control*** | 180 a | 10.16 | 0.20 a | 0.03 | 4.2 ab | 0.75 |

TABLE 1-continued

| Harvest year: 2000 (2nd leaf) | | | | |
|---|---|---|---|---|
| | Summer pruning weight (kg/tree)* | | Root suckers (number/tree) | |
| Rootstock | Mean | S.E.M. | Mean | S.E.M. |
| 94-94-5** | no data | | 0.0c | 0.0 |
| 94-94-10** | | | 0.6b | 0.1 |
| 94-94-32** | | | 0.0c | 0.0 |
| 94-94-48** | | | 0.0c | 0.0 |
| 94-94-50** | | | 0.0c | 0.0 |
| Control*** | | | 1.4a | 0.7 |

| Harvest year: 2001 (3rd leaf) | | | | | | |
|---|---|---|---|---|---|---|
| | Tree height (cm)* | | TCA (cm2)* | | Crop yield (kg/tree)* | |
| Rootstock | Mean* | S.E.M. | Mean | S.E.M. | Mean | S.E.M. |
| 94-94-10**** | 272.1 b | 18.59 | 27.6 b | 5.85 | 11.6 b | 2.23 |
| 94-94-32**** | 267.0 b | 19.17 | 23.0 b | 3.82 | 9.4 b | 1.52 |
| 94-94-50**** | 121.5 ab | 17.36 | 39.2 b | 4.19 | 14.2 b | 1.34 |
| Control | 380.5 a | 19.66 | 60.2 a | 6.09 | 24.4 a | 1.78 |

| Harvest year: 2001 (3rd leaf) | | | | | | |
|---|---|---|---|---|---|---|
| | Fruit weight (g/fruit) | | Cropping effi-ciency (Crop | | Winter pruning weight | |
| Rootstock | Mean* | S.E.M. | Mean | S.E.M. | Mean | S.E.M. |
| 94-94-10**** | 141.7 a | 7.52 | 0.43 a | 0.03 | 2.3 b | 0.92 |
| 94-94-32**** | 141.0 a | 5.70 | 0.44 a | 0.07 | 1.5 b | 0.43 |
| 94-94-50**** | 154.9 a | 5.39 | 0.40 a | 0.04 | 3.3 ab | 0.70 |
| Control | 147.0 a | 5.02 | 0.46 a | 0.03 | 5.8 a | 0.90 |

| Harvest year: 2001 (3rd leaf) | | | | |
|---|---|---|---|---|
| | Summer pruning weight (kg/tree)* | | Root suckers (number/tree) | |
| Rootstock | Mean | S.E.M. | Mean | S.E.M. |
| 94-94-10**** | no data | | 0.0b | 0.0 |
| 94-94-32**** | | | 0.0b | 0.0 |
| 94-94-50**** | | | 0.0b | 0.0 |
| Control | | | 0.8a | 0.9 |

| Harvest year: 2002 (4th leaf) | | | | | | |
|---|---|---|---|---|---|---|
| | Tree height (cm)* | | TCA (cm2)* | | Crop yield (kg/tree)* | |
| Rootstock | Mean* | S.E.M. | Mean | S.E.M. | Mean | S.E.M. |
| 94-94-10 | 345.0 b | 25.57 | 41.8 b | 8.01 | 19.7 b | 3.37 |
| 94-94-32 | 313.5 b | 27.76 | 30.4 b | 5.84 | 16.5 b | 1.89 |
| 94-94-50 | 357.7 b | 15.25 | 52.6 b | 5.19 | 22.2 ab | 2.11 |
| Control | 417.5 a | 12.55 | 77.4 a | 8.12 | 29.6 a | 2.60 |

| Harvest year: 2002 (4th leaf) | | | | | | |
|---|---|---|---|---|---|---|
| | Fruit weight (g/fruit) | | Cropping effi-ciency (Crop | | Winter pruning weight | |
| Rootstock | Mean* | S.E.M. | Mean | S.E.M. | Mean | S.E.M. |
| 94-94-10 | 179.2 a | 8.81 | 0.50 ab | 0.03 | 8.2 b | 2.32 |
| 94-94-32 | 180.3 a | 4.70 | 0.67 a | 0.13 | 5.4 b | 1.54 |
| 94-94-50 | 194.6 a | 6.89 | 0.44 b | 0.04 | 11.1 b | 1.42 |
| Control | 179.7 a | 11.48 | 0.46 b | 0.05 | 17.3 a | 1.97 |

TABLE 1-continued

| Harvest year: 2002 (4th leaf) | | | | |
|---|---|---|---|---|
| | Summer pruning weight (kg/tree)* | | Root suckers (number/tree) | |
| Rootstock | Mean | S.E.M. | Mean | S.E.M. |
| 94-94-10**** | 9.6 b | 3.5 | 0.0 b | 0.0 |
| 94-94-32**** | 10.4 b | 2.5 | 0.0 b | 0.0 |
| 94-94-50**** | 12.2 b | 2.2 | 0.0 b | 0.0 |
| Control | 21.8 a | 1.9 | 0.9 a | 0.5 |

| Harvest year: 2003 (5th leaf) | | | | | | |
|---|---|---|---|---|---|---|
| | Tree height (cm)* | | TCA (cm2)* | | Crop yield (kg/tree)* | |
| Rootstock | Mean * | S.E.M. | Mean | S.E.M. | Mean | S.E.M. |
| 94-94-10 | 387.5b | 41.0 | 54.6bc | 9.76 | 33.8 ab | 3.24 |
| 94-94-32 | 355.0b | 22.8 | 41.3c | 6.81 | 26.6 b | 2.96 |
| 94-94-50 | 407.7ab | 19.1 | 73.1ab | 5.54 | 38.0 ab | 1.61 |
| Control | 441.8a | 28.7 | 94.0a | 13.22 | 40.1 a | 2.62 |

| Harvest year: 2003 (5th leaf) | | | | | | |
|---|---|---|---|---|---|---|
| | Fruit weight (g/fruit) | | Cropping effi-ciency (Crop | | Winter pruning weight | |
| Rootstock | Mean * | S.E.M. | Mean | S.E.M. | Mean | S.E.M. |
| 94-94-10 | 190.6a | 9.51 | 0.68a | 0.08 | 4.1ab | 1.28 |
| 94-94-32 | 193.4a | 7.20 | 0.77a | 0.14 | 2.4b | 0.73 |
| 94-94-50 | 211.6a | 5.20 | 0.57a | 0.04 | 4.8ab | 0.50 |
| Control | 203.2a | 8.77 | 0.53a | 0.10 | 6.8a | 1.12 |

| Harvest year: 2003 (5th leaf) | | | | |
|---|---|---|---|---|
| | Summer pruning weight (kg/tree)* | | Root suckers (number/tree) | |
| Rootstock | Mean | S.E.M. | Mean | S.E.M. |
| 94-94-10 | 0.9b | 0.19 | 0.00b | 0.0 |
| 94-94-32 | 0.6b | 0.11 | 0.00b | 0.0 |
| 94-94-50 | 1.3b | 0.10 | 0.00b | 0.0 |
| Control | 2.3a | 0.55 | 0.9a | 0.5 |

*Means within column and year with the same letter(s) are not significantly different according to Duncan's Multiple Range Test P ? 0.05.
**Data were collected on these five HBOK rootstocks only, out of original eight, because the other three were tested to be susceptible to root-knote nematode.
***Control is the average of values of Nemaguard and Lovell rootstocks together.
****Data on these three HBOK rootstocks only were collected, starting in 2001, because these were the ones that showed promise as tree size-reducing rootstocks.

Resistance of Clonal Propagules to Root-Knot Nematode in Greenhouse Pot Tests

In 2006, reactions of clonal propagules of 94-94-10 ('HBOK 10'), 94-94-32 ('HBOK 32'), and 94-94-50 ('HBOK 50') to the root-knot nematode *M. incognita* (race 1) isolate 'Beltran' were recorded in a greenhouse pot test. Leafy cuttings were taken from each of the three mother trees and rooted. Cuttings were grown for ten months in a greenhouse then given a chilling treatment by growing outside for another two months. Each was repotted in sand while dormant, then grown for another month in a greenhouse before nematode inoculation. A single inoculation with the isolate was made following procedures for inoculum preparation and inoculation as described by Gillen (2001) on Mar. 15, 2006. The test was evaluated after about five months of incubation, on Aug. 9, 2006. Entire root systems of each cutting were scored for gall formation and rated according to system of Sherman et al. (1981).

The mean scores for entries in this experiment ranged from 0 (considered to be resistant) to 5.0 (susceptible) (Table 2). The two standards 'Lovell' and 'Nemaguard' had mean scores similar to what was expected based on their known reactions. Among the three experimental rootstocks, 94-94-50 ('HBOK 50') had a mean score of 0, slightly better than 'Nemaguard', while the scores of 94-94-10 ('HBOK 10') and 94-94-32 ('HBOK 32') were comparable to 'Nemaguard' (Table 2). These results were consistent with those obtained from the seedling screen conducted earlier by Gillen (2001).

Based on data over several years of trials at Davis, Calif., and Parlier, Calif., the mother trees, 94-94-10 ('HBOK 10'), 94-94-32 ('HBOK 32') and 94-94-50 ('HBOK 50') were chosen as sources of asexual propagules for additional field trials, planted in 2003 and 2004, to determine their potential as rootstocks for peach and nectarine.

The productivity of compound trees having peach and nectarine scion cultivars on 'HBOK 10', 'HBOK 32', and 'HBOK 50' and standard 'Nemaguard' were compared in several field trials in California. The results are summarized below.

Table 2 below shows Nematode reaction of rooted cuttings of selected clones of experimental lines compared to standard rootstocks 'Lovell' and 'Nemaguard' in greenhouse pot tests, conducted March-August, 2006.

TABLE 2

| Cultivar or clone | Number of plants | Mean score | S.E.M. |
|---|---|---|---|
| Lovell | 12 | 4.75 | 0.18 |
| Nemaguard | 12 | 0.17 | 0.11 |
| 28-3 | 12 | 3.58 | 0.62 |
| 29-31 | 13 | 0.23 | 0.12 |
| 94-94-10 | 12 | 0.17 | 0.11 |
| 94-94-32 | 12 | 0.33 | 0.14 |
| 94-94-50 | 12 | 0 | 0 |
| 2-6 | 12 | 5.0 | 0 |
| 3-6 | 12 | 1.0 | 0 |

Scores: 0 = no galls present on roots; 1 = 1 to 5 galls; 2 = 6 to 10 galls; 3 - 11-15 galls; 4 = 16 to 20 galls; and 5 = more than 20 galls.

Performance of 'HBOK 10', 'HBOK 32', and 'HBOK 50' in Field Trials

'HBOK 10', 'HBOK 32', and 'HBOK 50' rootstocks were among several studied in field trials. Data for only 'HBOK 50', the standard rootstock 'Nemaguard', and in some cases, other rootstocks where a comparison is meaningful, are presented. Data for all entries in the field trials are found in DeJong et al. (2005, 2006, 2007, and 2008).

Most of the propagation of these experimental materials for the field experiments was by leafy cuttings at Davis, Calif. Rooted materials were then potted and budded, with chosen scion cultivars, in greenhouses. Compound plants were provided during the winter for planting the following spring.

Performance of 'O'Henry' Peach Scion on Different Rootstocks

A field trial was established at Parlier, Calif., in February 2003 to measure growth and productivity of compound trees of which the scion cultivar 'O'Henry' peach was bud grafted onto different rootstocks, including 'HBOK 10', 'HBOK 32', and 'HBOK 50' for comparisons to the standard rootstock 'Nemaguard' and to others either being tested or in commercial use. A total of 20 trees of each rootstock/scion combination were planted and trained to the perpendicular V system. Between-row spacing of 5.49 m (18 ft) was the same for all rootstock/scion combinations, and in-row spacing was 2.13 m (7 ft) between trees for all treatments. Four replications of 5 trees each were arranged according to a randomized complete block design.

The soil at the site is a well-drained Hanford fine sandy loam. The trees were provided supplemental moisture with micro-sprinklers to maintain 100% of potential evapo-transpiration prior to harvest and about 80% after harvest. Supplemental nutrients were provided by applying UN 32 through irrigation at a rate of 5 gal per acre per application of 2 to 3 applications per year until the trees were 2 years old. Beginning in year three, 250 lb per acre of ammonium nitrate was applied each fall. Pesticides were applied according to standard horticultural practices. Weeds were controlled by mowing the row middles and applying herbicides to maintain a 1.5 m wide weed-free strip down the tree rows.

Trees were pruned in May and late November according to standard recommendations for growing the trees. Severity of pruning was adjusted according to the growth characteristics of each rootstock/scion combination to optimize crop production while developing/maintaining the desired tree shape. The first significant fruit set occurred in the third leaf and crop load was adjusted for tree size by hand thinning to maintain a minimum spacing between fruit. Because patterns of fruit maturity varied among rootstocks, fruit were harvested in several picks but data were combined from all harvests to calculate mean fruit yield. Data on crop load (fruit per tree) and fruit size were also recorded.

Results

The six rootstocks compared beginning at the $3^{rd}$-leaf (2005 harvest year) and continuing through the $6^{th}$-leaf had differences in tree height and TCA among the compound trees (Table 3). Trees on 'Nemaguard' were the largest throughout. Trees on 'HBOK 10' and 'HBOK 32' were smaller than 'Nemaguard' and similar to 'Ishtara', which is known for size controlling potential (Table 3). 'HBOK 50' was shorter than 'Nemaguard' except in harvest year 2007 and although the TCA was less than 'Nemaguard' each year, the difference was significant only in 2005 (Table 3). 'Cadaman' was included for comparison because it has a level of resistance to nematodes but as seen here, trees are of similar size to 'Nemaguard' (Table 3). 'Ishtara', which has some nematode resistance, showed reduced tree height and smaller TCA than 'Nemaguard'. 'Cadaman' is a peach×almond hybrid and 'Ishtara' a peach×plum hybrid.

Cropping efficiency of 'HBOK 10' and 'HBOK 32' was greater than of 'Nemaguard' in 2006 through 2008, but significant only for 'HBOK 32' (Table 3). Fruit weight was slightly less also. Each of the four years, the amount of material removed during both summer and dormant pruning from 'HBOK 10' and 'HBOK 32' was significantly less than from 'Nemaguard', and usually there was less pruned material from trees on 'HBOK 50' (Table 3). All three rootstocks produced significantly fewer root suckers than 'Nemaguard' each year.

Table 3 below shows mean values for tree height, trunk cross sectional area (TCA), crop yield, fruit weight, cropping efficiency, winter pruning weight, and summer pruning weight of third-leaf through sixth-leaf 'O'Henry' peach scions on six different rootstocks and mean number of root suckers on each of the rootstocks. Trees were planted at the Parlier, Calif., in 2003.

TABLE 3

| Harvest year 2005 (3rd leaf) | | | | | | |
|---|---|---|---|---|---|---|
| | Tree height (cm)* | | TCA (cm2)* | | Crop yield (kg/tree)* | |
| Rootstock | Mean* | S.E.M. | Mean | S.E.M. | Mean | S.E.M. |
| HBOK10 | 342 b | 9.1 | 43.4 c | 4.4 | 7.7 b | 1 |
| HBOK32 | 337 b | 7.1 | 33.9 d | 1.6 | 7.1 b | 1.7 |
| HBOK50 | 367 b | 2.4 | 58.7 b | 4.7 | 10.1 b | 1.5 |
| Nemaguard | 402 a | 5 | 68.8 a | 2.9 | 14.3 a | 1.5 |

TABLE 3-continued

| | | | | | | |
|---|---|---|---|---|---|---|
| Cadaman | 383 a | 7.1 | 59.9 b | 2.8 | 14.5 a | 1.7 |
| Ishtara | 333 b | 7.1 | 36.8 dc | 2.2 | 6.2 b | 0.6 |

Harvest year 2005 (3rd leaf)

| | Fruit weight (g/fruit)* | | Cropping efficiency (Crop yield/TCA)* | | Winter pruning weight (kg/tree)* | |
|---|---|---|---|---|---|---|
| Rootstock | Mean | S.E.M. | Mean | S.E.M. | Mean | S.E.M. |
| HBOK10 | 255 cd | 5.5 | 0.21 a | 0.04 | 4.1 b | 0.5 |
| HBOK32 | 250 d | 2 | 0.21 a | 0.05 | 2.4 c | 0.2 |
| HBOK50 | 251 d | 15.2 | 0.18 a | 0.03 | 4.3 b | 0.4 |
| Nemaguard | 268 cb | 7 | 0.21 a | 0.02 | 5.8 a | 0.1 |
| Cadaman | 283 b | 7.4 | 0.26 a | 0.03 | 5.6 a | 0.4 |
| Ishtara | 298 a | 5.9 | 0.17 a | 0.02 | 2.5 c | 0.2 |

Harvest year 2005 (3rd leaf)

| | Summer pruning weight (kg/tree)* | | Root suckers (number/tree)* | |
|---|---|---|---|---|
| Rootstock | Mean | S.E.M. | Mean | S.E.M. |
| HBOK10 | 1.1 c | 0.2 | 0.3 b | 0.1 |
| HBOK32 | 0.7 c | 0.1 | 0 b | 0 |
| HBOK50 | 0.9 c | 0.3 | 0.1 b | 0 |
| Nemaguard | 2.1 a | 0.2 | 3.8 a | 0.1 |
| Cadaman | 1.6 b | 0.1 | 4.4 a | 1 |
| Ishtara | 0.9 c | 0.1 | 0 b | 0 |

Harvest year 2006 (4th leaf)

| | Tree height (cm)* | | TCA (cm2)* | | Crop yield (kg/tree)* | |
|---|---|---|---|---|---|---|
| Rootstock | Mean* | S.E.M. | Mean | S.E.M. | Mean | S.E.M. |
| HBOK 10 | 428b | 9.2 | 52.7b | 4.3 | 24.1 c | 1.3 |
| HBOK 32 | 421 b | 8.1 | 46.2 b | 2.3 | 24.5 c | 0.7 |
| HBOK50 | 459 b | 5.2 | 73.4 a | 2.8 | 30.2 b | 1.1 |
| Nemaguard | 502 a | 4.1 | 82.9 a | 2.8 | 33.9 a | 0.8 |
| Cadaman | 479 ab | 6.2 | 73.5 a | 3.2 | 33.0 a | 0.4 |
| Ishtara | 416 b | 8.3 | 49.7 b | 2.9 | 29.5 b | 0.8 |

Harvest year 2006 (4th leaf)

| | Fruit weight (g/fruit)* | | Cropping efficiency (Crop yield/TCA)* | | Winter pruning weight (kg/tree)* | |
|---|---|---|---|---|---|---|
| Rootstock | Mean | S.E.M. | Mean | S.E.M. | Mean | S.E.M. |
| HBOK 10 | 191 bc | 2.8 | 0.49 bc | 0.04 | 5.7 b | 0.4 |
| HBOK 32 | 188 c | 5.1 | 0.55 ab | 0.03 | 3.4 c | 0.2 |
| HBOK50 | 192 b | 2.5 | 0.40 d | 0.02 | 6.4 b | 0.4 |
| Nemaguard | 206 a | 3.8 | 0.41 d | 0.01 | 8 a | 0.3 |
| Cadaman | 191 b | 5.7 | 0.45 dc | 0.02 | 8 a | 0.7 |
| Ishtara | 188 c | 2.1 | 0.59 a | 0.04 | 2.9 c | 0.1 |

Harvest year 2006 (4th leaf)

| | Summer pruning weight (kg/tree)* | | Root suckers (number/tree)* | |
|---|---|---|---|---|
| Rootstock | Mean | S.E.M. | Mean | S.E.M. |
| HBOK 10 | 0.5 b | 0 | 0.3 b | 0.1 |
| HBOK 32 | 0.3 c | 0.1 | 0 b | 0 |
| HBOK50 | 0.5 b | 0 | 0.1 b | 0 |
| Nemaguard | 0.6 a | 0 | 3.8 a | 0.1 |
| Cadaman | 0.7 a | 0 | 4.4 a | 1 |
| Ishtara | 0.2 d | 0 | 0 b | 0 |

TABLE 3-continued

Harvest year 2007 (5th leaf)

| | Tree height (cm)* | | TCA (cm2)* | | Crop yield (kg/tree)* | |
|---|---|---|---|---|---|---|
| Rootstock | Mean* | S.E.M. | Mean | S.E.M. | Mean | S.E.M. |
| HBOK 10 | 390 cb | 9.4 | 68.3 b | 5.7 | 45.1 c | 1.9 |
| HBOK 32 | 376 cd | 8.7 | 59.1 b | 3.3 | 50.8 b | 0.9 |
| HBOK50 | 424 a | 7.5 | 102.3 a | 5.3 | 58.0 a | 0.4 |
| Nemaguard | 432 a | 3.4 | 104.1 a | 4.3 | 60.4 a | 1.2 |
| Cadaman | 409 b | 5.8 | 100.2 a | 5.5 | 61.1 a | 0.8 |
| Ishtara | 361 d | 9.4 | 64.3 b | 3.6 | 47.6 bc | 2 |

Harvest year 2007 (5th leaf)

| | Fruit weight (g/fruit)* | | Cropping efficiency (Crop yield/TCA)* | | Winter pruning weight (kg/tree)* | |
|---|---|---|---|---|---|---|
| Rootstock | Mean | S.E.M. | Mean | S.E.M. | Mean | S.E.M. |
| HBOK 10 | 208.2 bc | 3.4 | 0.66 cb | 0.05 | 6.7 c | 0.2 |
| HBOK 32 | 194.5 c | 6.8 | 0.86 a | 0.05 | 6 d | 0.2 |
| HBOK50 | 199.8 c | 11.7 | 0.62 c | 0.04 | 9.4 ab | 0.7 |
| Nemaguard | 240.5 a | 5.2 | 0.58 c | 0.03 | 10.1 a | 0.3 |
| Cadaman | 220.2 b | 5.7 | 0.61 c | 0.03 | 8.4 b | 0.4 |
| Ishtara | 197.4 c | 1.7 | 0.74 b | 0.05 | 4.2 e | 0.1 |

Harvest year 2007 (5th leaf)

| | Summer pruning weight (kg/tree)* | | Root suckers (number/tree)* | |
|---|---|---|---|---|
| Rootstock | Mean | S.E.M. | Mean | S.E.M. |
| HBOK 10 | 2.6 b | 0.3 | 0.3 b | 0 |
| HBOK 32 | 1.9 cb | 0.4 | 0 b | 0 |
| HBOK50 | 4.0 a | 0.7 | 0.1 b | 0 |
| Nemaguard | 3.8 a | 0.6 | 4.1 a | 0.4 |
| Cadaman | 3.8 a | 0.5 | 4.1 a | 0.8 |
| Ishtara | 1 c | 0.2 | 0 b | 0 |

Harvest year 2008 (6th leaf)

| | Tree height (cm)* | | TCA (cm2)* | | Crop yield (kg/tree)* | |
|---|---|---|---|---|---|---|
| Rootstock | Mean* | S.E.M. | Mean | S.E.M. | Mean | S.E.M. |
| HBOK 10 | 425.6 c | 9.8 | 83.5 b | 6.6 | 45.7 d | 1.1 |
| HBOK 32 | 383.6 d | 6.8 | 73.2 b | 3.9 | 47.7 dc | 2.2 |
| HBOK 50 | 450 b | 6.1 | 111.6 a | 6 | 50.4 c | 1.3 |
| Nemaguard | 490.9 a | 9.7 | 119.9 a | 4.7 | 56.5 b | 0.9 |
| Cadaman | 462.7 b | 8.9 | 112.9 a | 5.3 | 62.2 a | 1.5 |
| Ishtara | 394.7 d | 6.8 | 71.2 b | 3.7 | 41.2 e | 1.3 |

Harvest year 2008 (6th leaf)

| | Fruit weight (g/fruit)* | | Cropping efficiency (Crop yield/TCA)* | | Winter pruning weight (kg/tree)* | |
|---|---|---|---|---|---|---|
| Rootstock | Mean | S.E.M. | Mean | S.E.M. | Mean | S.E.M. |
| HBOK 10 | 205 b | 5.9 | 0.59 ab | 0.04 | 5.8 c | 0.4 |
| HBOK 32 | 218.7 b | 4.6 | 0.67 a | 0.03 | 4.4 d | 0.27 |
| HBOK 50 | 216.4 b | 5.4 | 0.46 c | 0.02 | 7 b | 0.5 |
| Nemaguard | 221.7 ab | 5.4 | 0.48 c | 0.02 | 8.9 a | 0.3 |
| Cadaman | 235.2 a | 6.5 | 0.56 b | 0.02 | 8.5 a | 0.4 |
| Ishtara | 207.5 b | 6.6 | 0.6 ab | 0.03 | 2.1 e | 0.2 |

TABLE 3-continued

| | Harvest year 2008 (6th leaf) | | | |
|---|---|---|---|---|
| | Summer pruning weight (kg/tree)* | | Root suckers (number/tree)* | |
| Rootstock | Mean | S.E.M. | Mean | S.E.M. |
| HBOK 10 | 0.5 bc | 0.05 | 0.3 b | 0 |
| HBOK 32 | 0.3 dc | 0.05 | 0 b | 0 |
| HBOK 50 | 0.81 a | 0.07 | 0.1 b | 0 |
| Nemaguard | 0.65 ab | 0.1 | 4.4 a | 0.4 |
| Cadaman | 0.64 ab | 0.09 | 4.1 a | 0.8 |
| Ishtara | 0.13 d | 0 | 0.1 b | 0 |

*Means within column and year with the same letter(s) are not significantly different according to Duncan's Multiple Range Test P ≦ 0.05.

Discussion

In this trial 'HBOK 10' and 'HBOK 32' showed consistent measures of tree height and TCA that are indicative of size controlling rootstocks for peach. Although compound plants with 'HBOK 50' were smaller than the checks in the previous trial with 'O'Henry' scions and generally so in this trial, the differences were not always significant.

The 'HBOK 50' rootstock appears to give a small reduction in size, which may make it be more appropriate for use as a rootstock for almond scions, since both 'HBOK 10' and 'HBOK 32' would give too great of a reduction. Also the root-knot nematode resistance of 'HBOK 50' would be valuable if used with an almond scion.

Nematode Response of Rootstocks in Field Trials

Trees of 'HBOK 10' and 'HBOK 50' were determined to be heterozygous resistant and 'HBOK 32' homozygous resistant to root-knot nematodes based on reactions of OP-$F_3$ progeny seedlings from each inoculated with nematodes (Gillen, 2005) and levels of resistance comparable to 'Nemaguard' were confirmed in subsequent pot tests. Although field tests were not conducted to determine reaction to root-knot nematode, available data from other sources describe 'HBOK' rootstock response to root knot nematode and other nematodes that infest roots of *Prunus* crops.

Clonal propagules of these rootstocks have been included in several field trials conducted at Parlier, Calif., and other sites. The results of a nematode screening field trial conducted in 2004 are shown in Table 4 below. 'HBOK 10' and 'HBOK 32' had levels of response to root-knot nematode similar, but slightly less resistant than 'Nemaguard'. 'HBOK 50' showed no symptoms in the single repetition in that trial.

Table 4 below shows the response (nematodes/g root, fw) of six rootstocks to root lesion and root-knot nematodes in field trials during 2004.

TABLE 4

| | Root lesion only | | Root-knot only | | Root lesion and Root-knot | |
|---|---|---|---|---|---|---|
| Rootstock | Mean | S.E.M. | Mean | S.E.M. | Mean | S.E.M. |
| HBOK 10 | 0.03 | 0.02 | 0.09 | 0.07 | 0.12 | 0.09 |
| HBOK 32 | 0.91 | 0.79 | 0.77 | 0.71 | 1.68 | 0.88 |
| HBOK 50 | 0.35[a] | — | 0 | — | 0.35 | — |
| Nemaguard | 0.72 | 0.35 | 0 | 0 | 0.7 | 0.35 |
| Cadaman | 0.01 | 0.01 | 0 | 0 | 0.01 | 0.01 |
| Ishtara | 22.46 | 4.12 | 0.02 | 0.02 | 22.48 | 4.1 |

The field trial included planting out 20 seedlings into an open field of Hanford sandy loam soil. Six seedlings were inoculated with root knot by itself, 6 were inoculated with root lesion by itself and the remaining 8 were inoculated with the combination of the two nematodes but from a different source that came from a 'Nemaguard' replant setting. If four or five more seedlings were available, and if adequate space was available, the four or five seedlings were planted into sandy soil containing ring nematode plus a single 'Nemaguard' adjacent to each of the five. Tree roots and aboveground biomass were assessed by using a backhoe to exhume the entire tree, usually at 6 months 12 months, and 18 months after planting. Young roots were collected from all along each root system. A 20 gram sample of diced root tips was placed in a funnel within a mist chamber for five days and nematodes forced to migrate through tissue paper into the test tubes. Nematodes were counted and identified as to species. The population of root-knot, *Meloidogyne incognita* was aggressive, the population of root lesion, *Pratylenchus vulnus* was moderately aggressive, and the population of ring nematode, *Criconemoides xenoplax* was moderately aggressive.

Additional data suggests that these three rootstocks have useful resistance to root-knot nematode and possibly to other nematodes as well. In "A Report to the California Tree Fruit Agreement—A greater number of rootstock choices can provide a partial alternative to methyl bromide fumigation " (McKenry, Dec. 30, 2007) it states, "One selection, 'HBOK-10', was as resistant to root-knot as 'Nemaguard' but supported half the number of root-lesion as 'Nemaguard'." In 2008, McKenry reported that 'HBOK 10' showed only 0.08 root-knot nematodes per gram of root compared to 0 for 'Nemaguard', 'Okinawa', 'Cadaman', and 'Ishtara', and 31 for 'Lovell' (McKenry, 2008). In the same report, a 2-year study showed few or no root-knot nematodes on 'HBOK 10' and 'HBOK 50', respectively, the latter being similar to 'Nemaguard'. There were few root lesion nematodes *Pratylenchus vulnus* per gram of root on 'HBOK 10', similar to numbers on 'Nemaguard', 'Lovell', 'Okinawa', 'Cadaman' and 'Ishtara', while 'HBOK 50' had higher levels than 'Nemaguard' (McKenry, 2008). In a field trial in Stanislaus County, Calif., 'HBOK 32' roots had fewer ring nematodes and root lesion nematodes and a similar amount of root-knot nematodes than 'Nemaguard' (McKenry, 2007).

Based on the seedling responses, ratings made in a pot test and the limited field studies, it is believed that 'HBOK 10', 'HBOK 32', and 'HBOK 50' have useful levels of resistance to root-knot nematode. The observations reported by McKenry suggest that they may have useful levels of resistance to some other nematodes.

Propagation of 'HBOK 10', 'HBOK 32', and 'HBOK 50' for Rootstocks

Asexual propagation of peach rootstock planting materials is usually peformed by one of three methods: leafy cuttings, hardwood (dormant) cuttings and tissue culture. Most of the propagation of these experimental materials for the field experiments was by leafy cuttings at Davis, Calif.

Propagation Via Leafy Cuttings

Materials were propagated using leafy cuttings. Stems were collected from June through August. They were cut into segments 6 to 10 inches long and the leaves near the base stripped away. Cuttings were then dipped in 1000 ppm IBA (dissolved in 50% ethyl alcohol) for five seconds and the base then placed in a soil-less mix of 1 part vermiculite and 2 parts perlite in propagation flats. Flats were placed under mist, with the frequency of misting regulated by an artificial leaf. Rooting occurred in about two to three weeks.

Propagation Via Hardwood (Dormant) Cuttings

Materials were propagated using hardwood cuttings. Current year shoots were collected in the middle of November. They were cut to 14 inch long and the basal ends soaked for 24 hours in a 100 ppm IBA. They were then placed in moist burlap bags, which were then placed in plastic bags, securely closed with a wire, and incubated at about 60° F. Cuttings were inspected every week starting after the second week of incubation. When the bases of most cuttings were covered with callus, they were planted in paper sleeves with soil-less mix of three parts fir bark and one part sand. They were placed under cover to protect from rain and watered whenever needed.

Propagation Via Tissue Culture

Materials were propagated using tissue culture. The procedures involved collecting young shoots, usually in April, and then sterilizing them with a surface sterilizing agent such as common household bleach. The shoots were then rinsed several times with sterile water, cut into small pieces each containing vegetative terminal or auxiliary buds. These cuttings were then placed in special media for tissue establishment. They were transferred into shoot multiplication medium where auxiliary shoots proliferate in numbers dependent on the type of rootstock. These multiplied shoots were cut and placed in a rooting medium to produce complete plants. The plants were taken out from the test tubes, where they were grown in the laboratory, placed in trays with soil-less mix and transferred into a greenhouse with fogging system for hardening. These were individually potted and transferred to a regular greenhouse where they were budded with different *Prunus* tops, grown till winter, and sold to farmers.

BOTANICAL DESCRIPTION OF THE PLANT

An experimental population (referred to as 'OP-$F_2$ population') derived from open pollination in 1994, of a single $F_1$ plant (No. P248-139) of the cross 'Harrow Blood' (HB)× 'Okinawa' (OK) was subsequently brought to Davis, Calif. The rootstock 'HBOK 50' resulted from a single plant (94-94-50) selected from that population at Davis, Calif. and subsequently propagated asexually to be studied as a rootstock.

The following horticultural description was developed from plant material of this new rootstock cultivar growing at Davis, Calif. Trees of 'HBOK 50' were observed for description during 2008 growing season. At that time, the trees were growing for the twelfth year. Color definition used throughout the following botanical description of this rootstock was set by Munsell Color Chart for Plant Tissues standards.

Tree:

*Tree.*—The tree from which this description is taken was grafted on 'Nemared' and planted at the Davis, Calif., in 1996. It was used as a source from which to propagate the new rootstock for experimental tests and plantings. The propagated tree was grown in a V-shaped training system for two years. Since then, the tree has received rather severe annual pruning to keep it in a highly vegetative state. The heavy pruning favors the development of many long straight shoots especially suited for the production of clonal rooted cuttings (FIG. 1). The trees of the subject new cultivar are vigorous and hardy under typical Sacramento Valley, Calif. climatic conditions.

Figure 2:
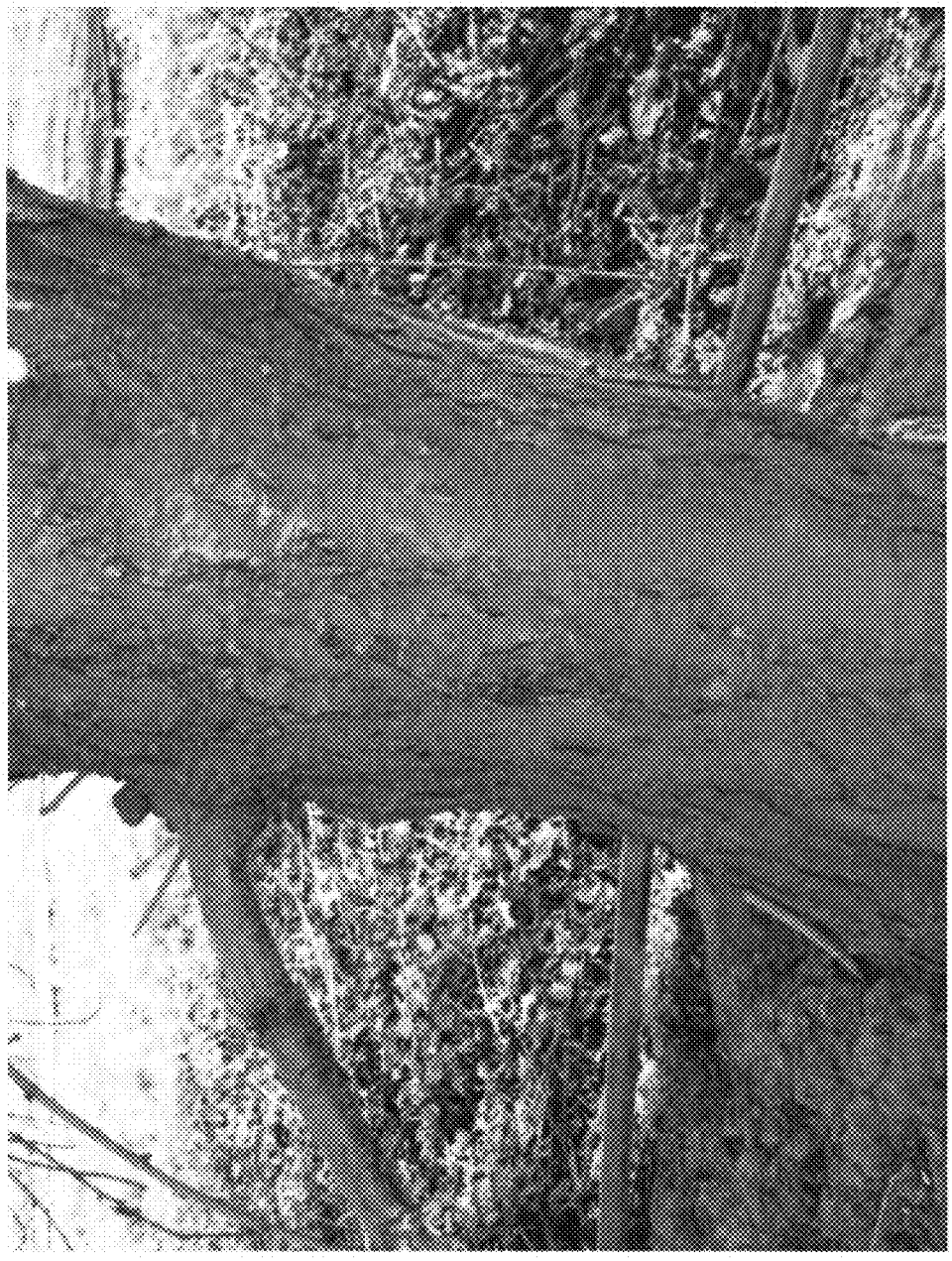
FIG. 2 shows the trunk of 'HBOK 50' grafted on 'Nemared' rootstock. The graft union here is indistinguishable.

Trunk:

*Trunk.*—The 'HBOK 50' scion was grafted on 'Nemared' rootstock and the union between the two peach accessions was so complete that the point of the graft union, after twelve years, was undistinguishable (FIG. 2). The circumference of the 'HBOK 50' trunk, 20 cm above the soil level, averages 64 cm. The trunk surface is coarse and has moderate number of cracks. Trunk color is green yellow (2.5 GY7/2 by Munsell Color Chart for Plant Tissues standards).

Figure 3:
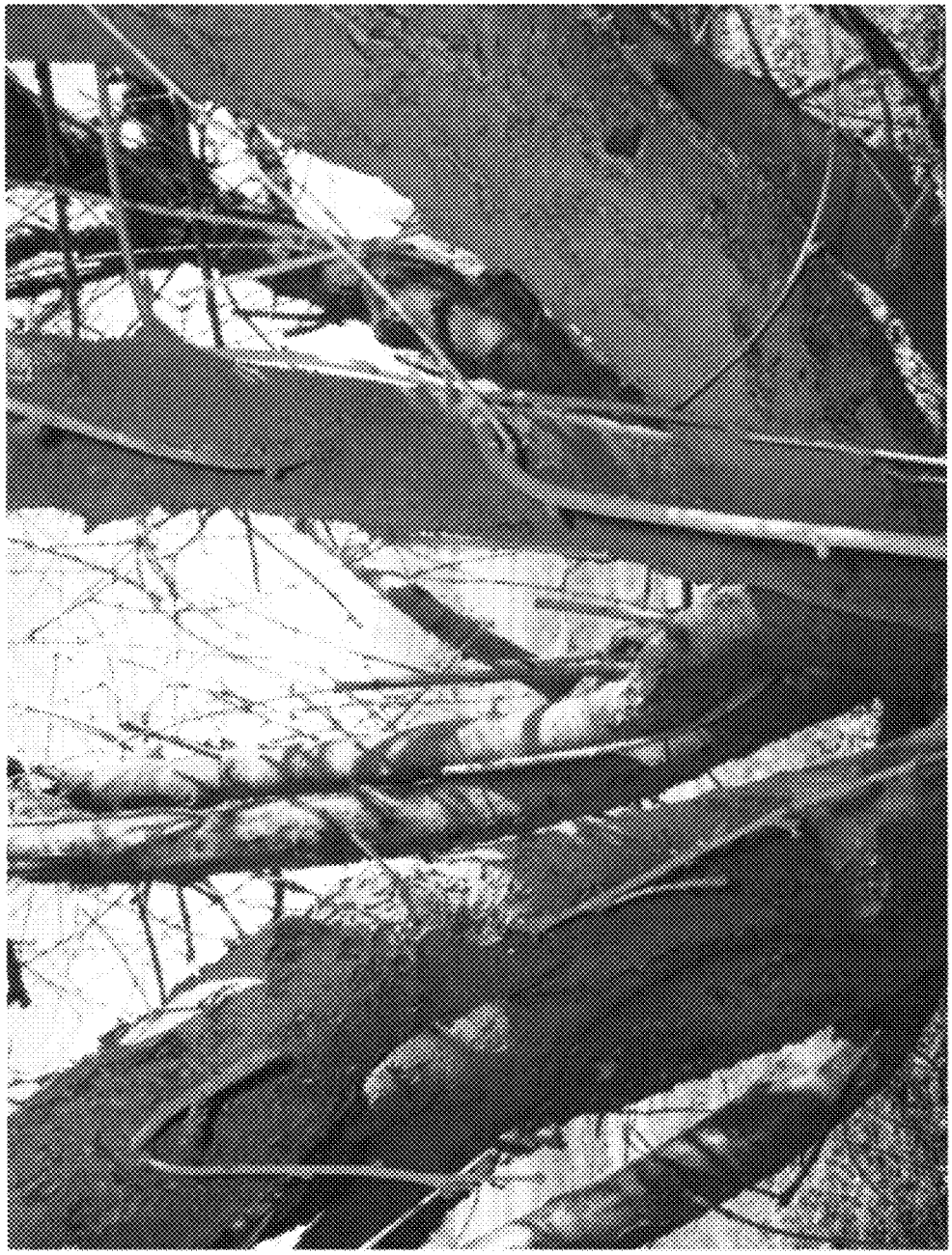
FIG. 3 shows the trunk, scaffolds, and upper spreader branches of 'HBOK 50' grafted on 'Nemared' rootstock. The green color on the scaffolds is caused by algae growth, since the picture was taken in the cool wet winter.
Figure 4:
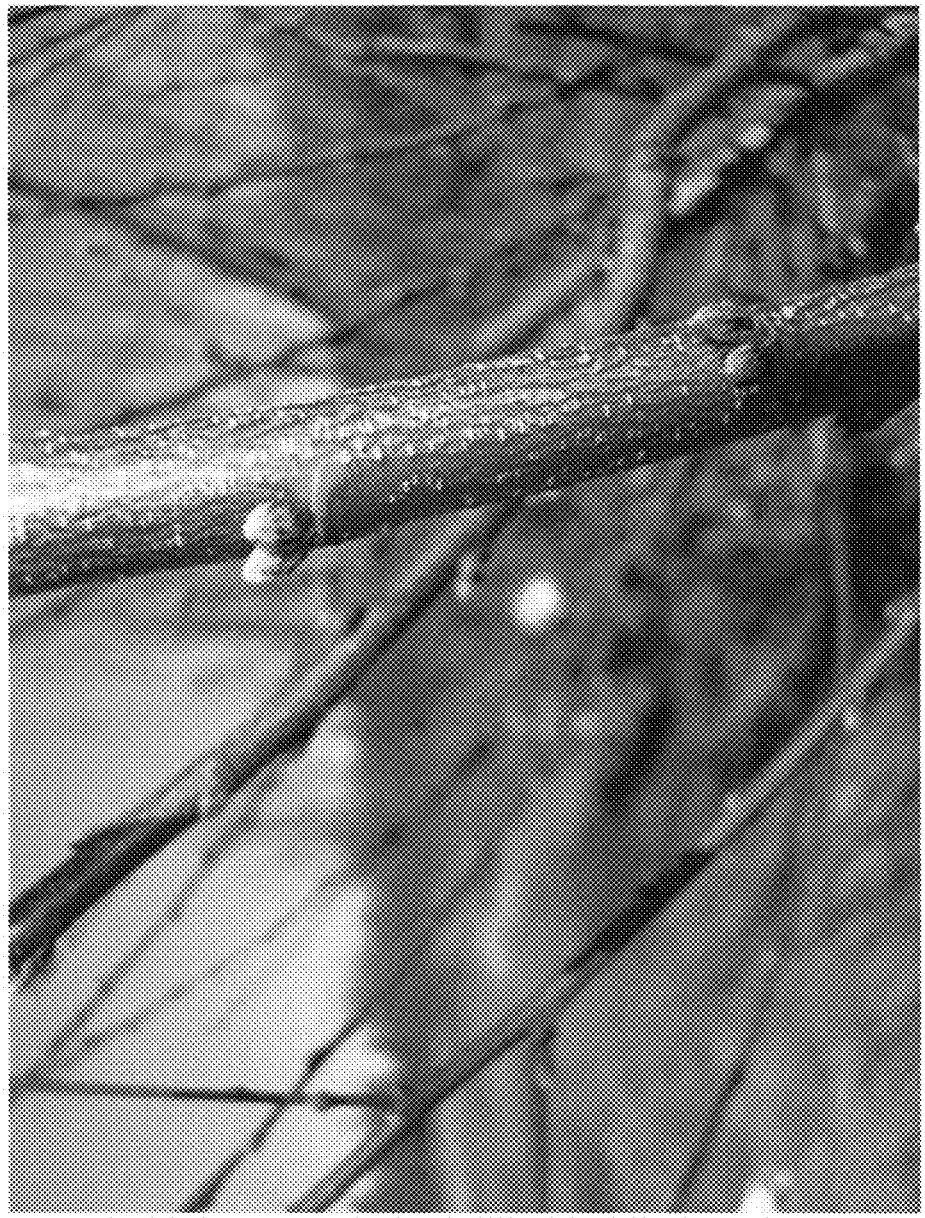
FIG. 4 shows small and flattened bark lenticels from 'HBOK 50' wood. Bark lenticels are present on two to four year old wood of 'HBOK 50'.

Branches:

*Branches.*—The tree branches have the normal thickness of a peach. The primary scaffolds arising from the trunk range from 30 to 35 cm in circumference measured at the base. Color of the main scaffolds is yellow red (2.5YR 7/2 Munsell Color Chart for Plant Tissues standards). Base circumference of upper spreader limbs ranges from 10 to 13 cm (FIG. 3). Lower and smaller fruit hangers wood bases range from 1.5 to 2 cm in circumference. Older branch surfaces are netted and lightly furrowed. Surface color of four year old branches ranges from red (2.5R 4-11 to 2.5R5-4 by Munsell Color Chart for Plant Tissues standards). Numerous small and flattened bark lenticels are present in two to four year old wood and absent on one year and older than four year old wood (FIG. 4). Lenticels range from 0.5 to 1 mm in width and 2 mm in length. Their color is yellow red (7.5YR 8/2 by Munsell Color Chart for Plant Tissues standards).

Figure 5:
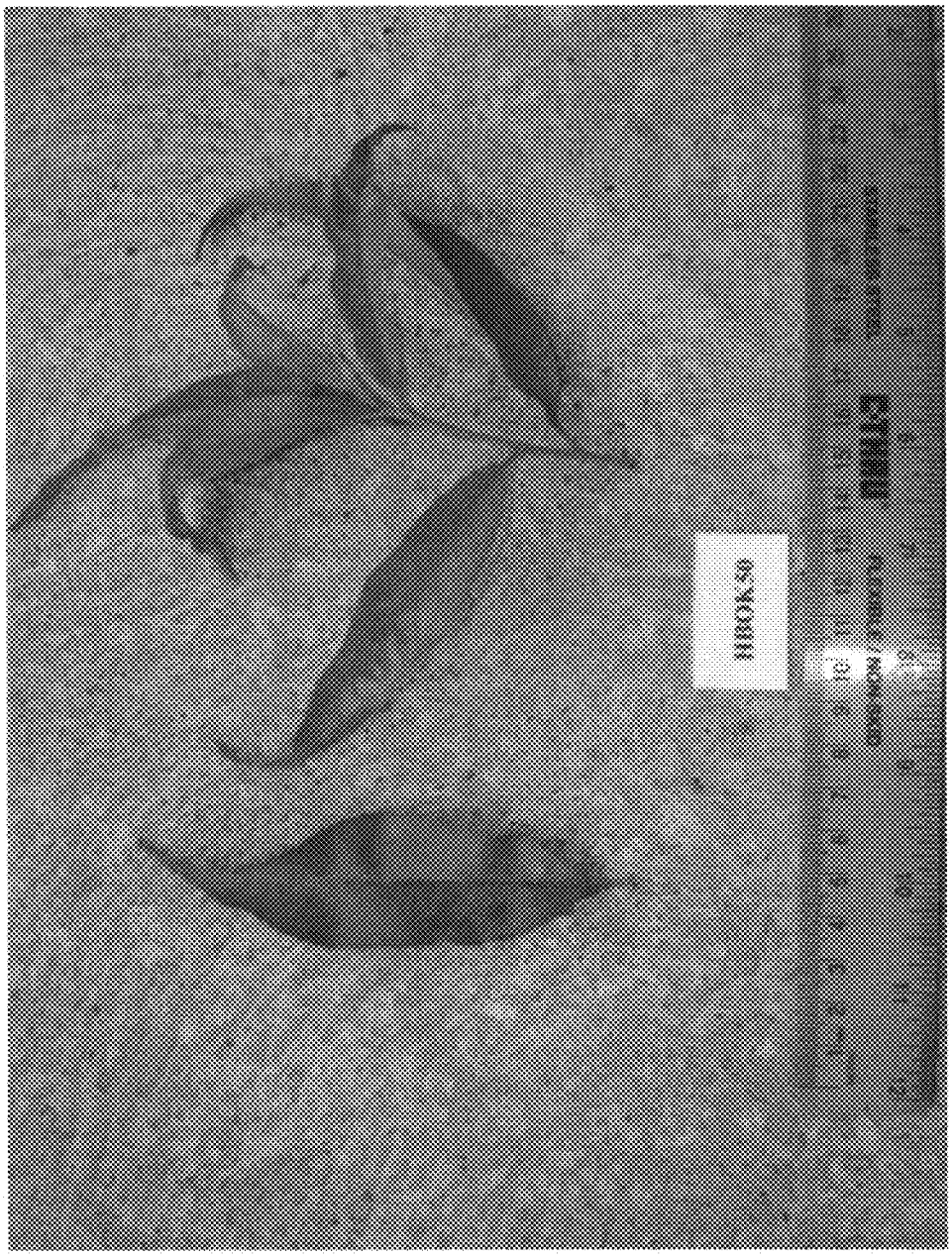
FIG. 5 shows a terminal piece of a branch of 'HBOK 50' showing newly made leaves.

Leaves:

*Leaves.*—The length of leaves, selected from the middle of shoots bearing fruits, ranges between 11 to 12 cm including the petiole and the width, measured at the widest point, is 3 cm in average. Leaf shape is subulate, the tip is acuminate, the base is acute, the venation is netted and the surface is glabrous (FIG. 5).

*Leaf Margins*—Leaf margin is serrulate and at the tip of each indentation there is a protrusion that resembles a small spine with a red color (2.5R-4/8 set by Munsell Color Chart for Plant Tissues standards). The color of the top of the leaf, in mid July, is green yellow (5GY 4-4 set by Munsell Color Chart for Plant Tissues standards)., and the color of the bottom of the leaf, in mid July is green (5GY 4-6 set by Munsell Color Chart for Plant Tissues standards). The leaf petiole is of average size. The color of the leaf petiole is green yellow (5GY 6-4 set by Munsell Color Chart for Plant Tissues standards). The length of the petiole is 10 mm and the thickness is 1 mm. The leaf petioles are glabrous. There are no stipules at the base of the petiole. There are an average of two reniform shaped leaf glands per leaf located on the petiole portion closest to the leaf blade. The color of the leaf glands is red (2.5 R 5/4 set by Munsell Color Chart for Plant Tissues standards).

Figure 6:
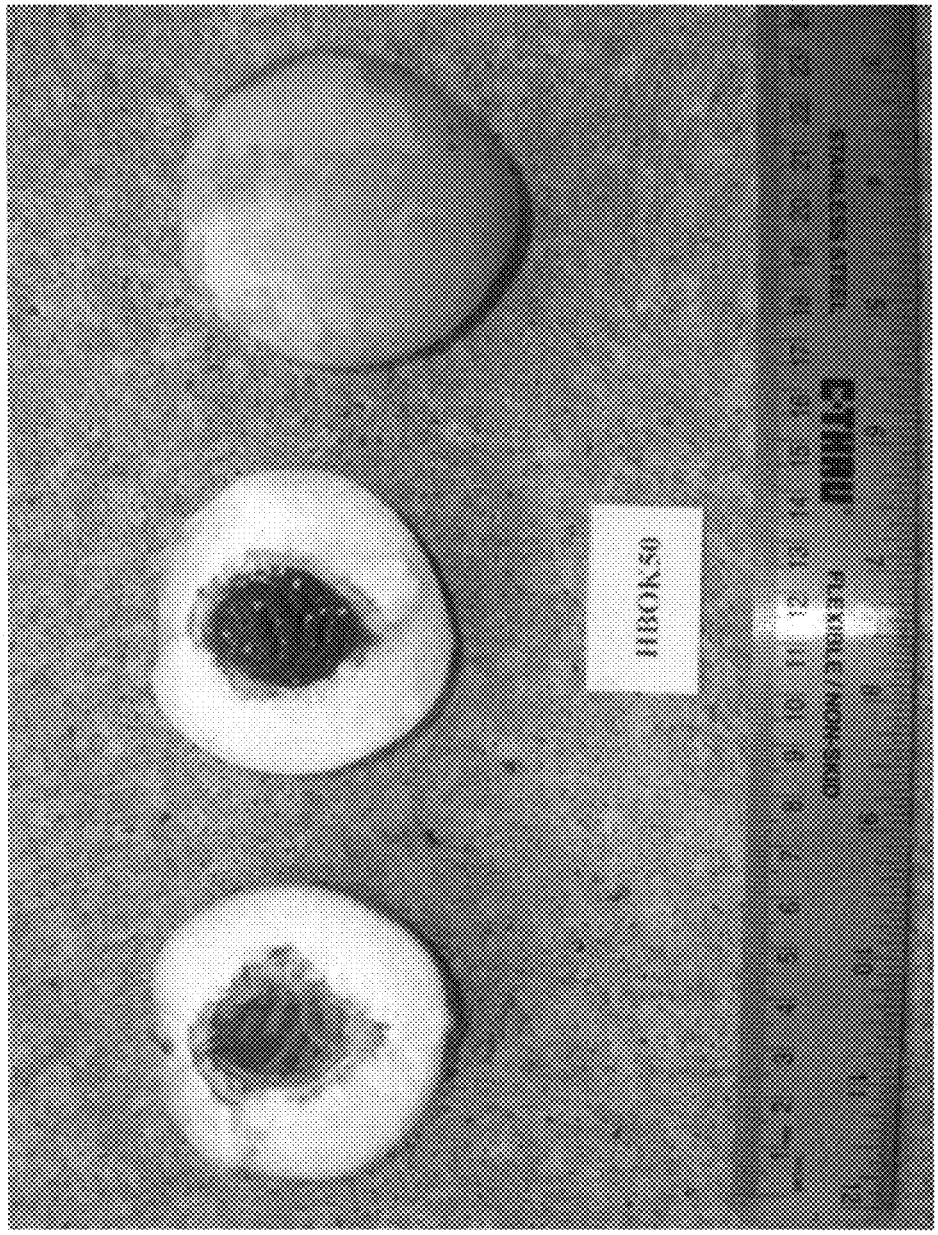
FIG. 6 shows fruits of the 'HBOK 50' rootstock.

Fruit:

*Fruit.*—The fruit is free stone. They ripen in the last week of July to the first week of August in Davis, Calif. Their surface, resembling a typical peach, is pubescent. Their shape is round with length equal to the width ranging from 50 to 60 mm. The tree produces an abundance of fruits and may break branches if not thinned. The color of fruit skin is green yellow (GY 21-2 set by Munsell Color Chart for Plant Tissues standards)-(FIG. 6). The color of the fruit when the fruit is between mature and ripe is yellow green (22-1 set by Munsell Color Chart for Plant Tissues standards). The color of the flesh adjacent to the seed is reddish (2.5R-5/10 set by Munsell Color Chart for Plant Tissues standards).

Seed:

*Seed.*—The seed (pit), resembling a typical peach seed, is ovate in shape with protrusion at the tip and deep grooves on the surface. The length, including the protrusion, is 30 to 35 mm and the width is 20 to 25 mm. The color is yellow red (7.5 YR 4-4 set by Munsell Color Chart for Plant Tissues standards)—(FIG. 6). The kernel of the seed is ovate with a length of 15 mm and a width of 12 mm. The color of the kernel is yellow red (5 YR 6/8). Resembling a typical peach seed kernel, it is bitter in taste.

Figure 7:
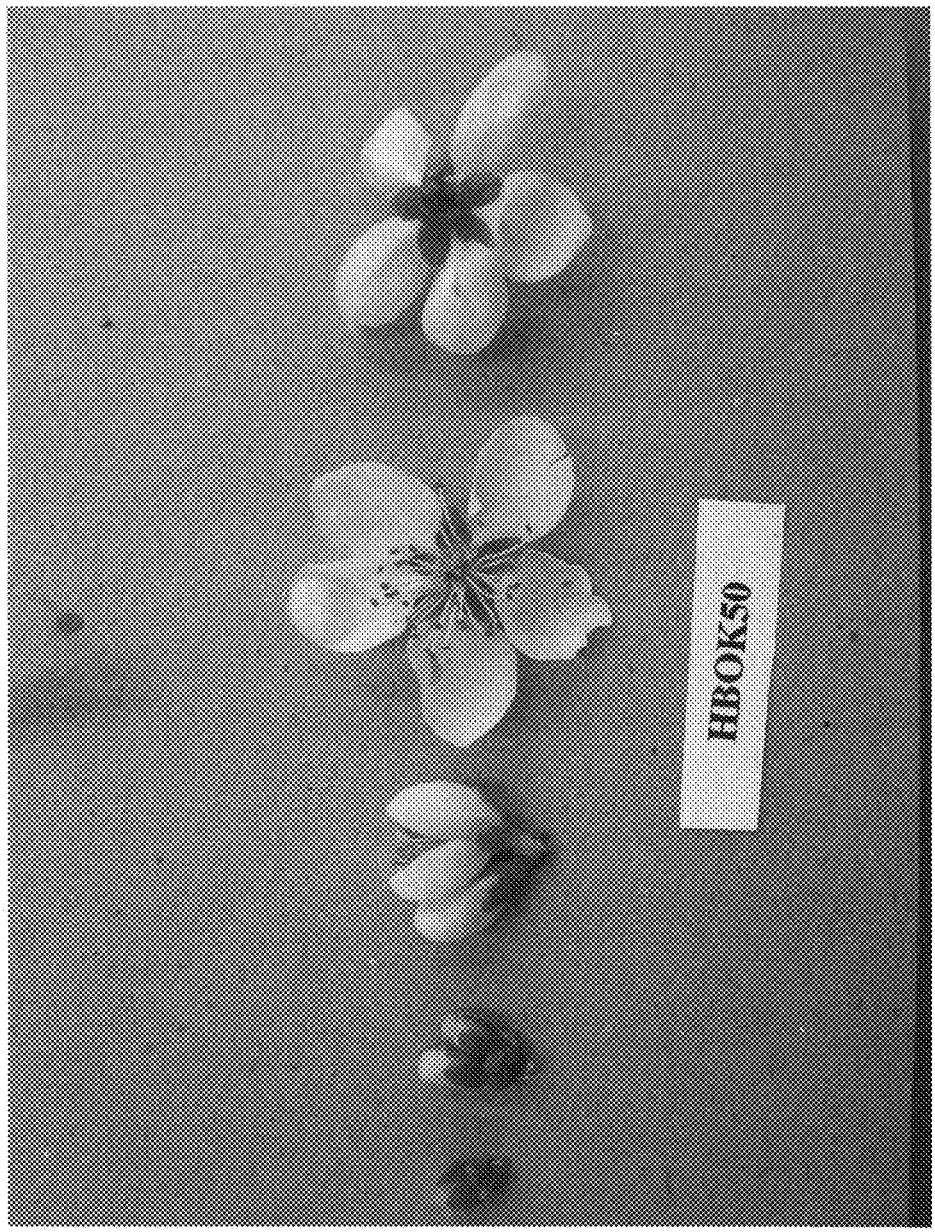
FIG. 7 shows flowers and flower buds of the 'HBOK 50' rootstock at different stages.

Floral Description:

*Flower buds.*—The flower buds are medium in size, 5 mm in length and 3.5 mm in width when first swelling (FIG. 7). One flower bud is usually born on each side of a vegetative bud. One vegetative bud is born on each node of one-year old wood. The flower buds are conic in form and relatively plump. The buds are hardy under typical Sacramento Valley, Calif. climatic conditions. Bud scales are red (2.5R-4-4) set by Munsell Color Chart for Plant Tissues standards (FIG. 7). The surfaces of the buds are heavily pubescent on the margins of the bud scales and gradually less in pubescence towards the center of the bud scales. The center of the bud scales is slightly pubescent.

*Blooming time.*—The time of the bloom is early in relation to standard commercial peach cultivars grown in the Sacramento Valley, Calif. climatic conditions. Average date of bloom is February 19. Average date of full bloom is March 1st. The start of vegetative bud break coincides with full bloom.

*Flower size.*—Average flower diameter, in a fully expanded condition, is 40 mm (FIG. 7).

*Bloom quality.*—Bloom quantity is heavy when compared with standard commercial peach cultivars grown in the Sacramento Valley, Calif. climatic conditions. The number of flower buds per node ranges from 1 to 3 with an average of two being most common. Many of the flower buds are retained on the tree to full bloom.

*Flower petals.*—The number of the petals per flower is five. The length of the flower petal is 20-25 mm and the width is 15-17 mm, in a fully expanded flower (FIG. 5). The shape of the petals is orbicular with margins that are entire. Each of the petals has nine main ribs palmate with net arranged veins. The petal color is pink (2.5R-9/3 set by Munsell Color Chart for Plant Tissues standards), with color intensifying (2.5R-8/5) towards the base.

*Flower pedicels.*—The length and the width of each of the flower pedicel and calyx, in a fully expanded flower, is 1 mm each. The color of the pedicel and the calyx is green yellow (2.5GY-7/8 set by Nickerson Color Fan standards)—(FIG. 7). The surface of the pedicel is glabrous.

*Sepals.*—The number of the sepals is five. The surfaces of the sepals are heavily pubescent on the margins of the bud scales and gradually less in pubescence towards the center of the bud scales. The center of the bud scales is slightly pubescent. The form is conic with a round apex. The width of the upper part, measured at the middle point, is 4 mm; the lower part is 2 mm. The color of the sepals, in a fully expanded flower, is red (2.5R-4/6 set by Munsell Color Chart for Plant Tissues standards)—(FIG. 7). The lower section of the sepals, from the early stages of the popcorn state to fully expanded flowers, has red dots. The color of the dots is the same as the sepals at the fully expanded state of the flower.

*Anthers and pollen.*—The size is of the anthers is average. During the popcorn stage of flower bud development, the color is red (5R-5/10 set by Munsell Color Chart for Plant Tissues standards) dorsally and around the edges ventrally (FIG. 7). Pollen is viable and medium in availability. Pollen color is yellow (2.5Y-8/12 set by Munsell Color Chart for Plant Tissues standards).

*Stamens.*—The average number of stamens is 40. Stamen length is variable, from 11 to 19 mm in a fully expanded flower. Color of stamen is red (2.5R-8/4 set by Munsell Color Chart for Plant Tissues standards)—(FIG. 7).

*Pistil.*—The pistil length is 18 to 20 mm. The pubescent ovary is 2 mm in length with a width of 1 mm; the style length is 18 mm with 0.3 mm width; and the stigma's length is 0.5 mm and with a width of 0.2 mm. The color of the style is yellow (7.5Y-9/8 -set by Munsell Color Chart for Plant Tissues standards). The color of the ovary, after removing the pubescence, is green yellow (2.5GY-6/8 set by Munsell Color Chart for Plant Tissues standards).

Summary

The new 'HBOK 50' rootstock, a hybrid between two peach parents, is useful as a commercial under-stock for peach and nectarine and perhaps, almond cultivars. The stock has been successfully propagated clonally by leafy cuttings and tissue culture. This rootstock imparts significant vigor control to the scion cultivar that is propagated on top of it. This rootstock produces very few root suckers, its anchorage is good and it is resistant to root-knot nematode. Utilization of adapted growth controlling rootstocks in commercial orchard situations reduces the height of the tree and the amount of wood pruned in the winter and summer, without compromising the quality of the fruit. This in turn increases the efficiency of various cultural operations such as pruning, thinning and harvesting by reducing the need for workers in the field to use tall ladders when carrying out these operations.

The following references are incorporated by reference for the purpose of providing further comparative data related to the claimed plant material.

Bliss, F.A., A.A. Almehdi, A.M. Dandekar, P.L. Schuerman and N. Bellaloui. 1999. Crown gall resistance in accessions of 20 *Prunus* species. HortScience 34(2):326-330.

DeJong, T., A. Almehdi, S. Johnson and K. Day. 2005. Improved rootstocks for peach and Nectarine. California Tree Fruit Agreement, Annual Report—2005. 20 pp.

DeJong, T., A. Almehdi, S. Johnson and K. Day. 2006. Improved rootstocks for peach and Nectarine. California Tree Fruit Agreement, Annual Report—2006. 18 pp.

DeJong, T., A. Almehdi, S. Johnson and K. Day. 2007. Improved rootstocks for peach and Nectarine. California Tree Fruit Agreement, Annual Report—2007. 19 pp.

DeJong, T., A. Almehdi, S. Johnson and K. Day. 2007. Improved rootstocks for peach and Nectarine. California Tree Fruit Agreement, Annual Report—2008. 19 pp.

DeJong, T., A. Almehdi, J. Grant and R. Duncan. 2004. Evaluation of rootstocks for tolerance to bacterial canker and orchard replant conditions. Cling Peach Annual Report—2004. 11pp.

DeJong, T., A. Almehdi, J. Grant and R. Duncan. 2005. Evaluation of rootstocks for tolerance to bacterial canker and orchard replant conditions. Cling Peach Annual Report—2005. 16 pp.

DeJong, T., A. Almehdi, J. Grant and R. Duncan. 2006. Evaluation of rootstocks for tolerance to bacterial canker and orchard replant conditions. Cling Peach Annual Report—2006. 15 pp.

Dirlewanger, E., E. Graziano, T. Joobeur, F. Garriga-Caldere, P. Cosson, W. Howard and P. Arús. 2004. Comparative mapping and marker assisted selection in Rosaceae fruit crops. Proc. Natl. Acad. Sci. USA 101:9891-9896.

Foolad, M.R., S. Arulsekar, V. Becerra, F.A. Bliss. 1995. A genetic map of *Prunus* based on an interspecific cross between peach and almond. Theor. Appl. Genet. 91:262-269.

Gillen, Anne M. 2001. Developing a Size-controlling and Root-knot Nematode Resistant Peach [*Prunus persica* (L.) Batsch] Rootstock. Ph.D. Dissertation, University of California, Davis. 237 pp.

Gillen, Anne M. and F.A. Bliss. 2005. Identification and mapping of markers linked to the Mi gene for root-knot resistance in peach. J. Amer. Soc. Hort. Sci. 130:24-33.

Howad, W., T. Yamamoto, E. Dirlewanger, R. Testolin, P. Cosson, G. Cipriani, A. J. Monforte, L. Georgi, A.G. Abbott. 2005. Mapping with a few plants: using selective mapping for microsatellite saturation of the *Prunus* reference map. Genetics 171:1305-1309.

McKenry, M. Dec. 30, 2007. A greater number of rootstock choices can provide a partial alternative to methyl bromide fumigation. A Report to the California Tree Fruit Agreement.

McKenry, M. 2008. Development of nematode/rootstock profiles for 40 rootstocks with the potential to be alternatives to 'Nemaguard'. California Almond Board, 2007 Conference Proceedings.

Ogundiwin, E.A., C.P. Peace, T.M. Gradziel, D.E. Parfitt, F.A. Bliss and C.H. Crisosto. 2009. A fruit quality gene map of *Prunus*. BMC Genomics (In review).

Sherman. W. B., Paul M. Lyrene and P. E. Hansche. 1981. Seedling Peach Rootstocks Resistant to Root-knot Nematodes. HortScience 16:523-524.

Westwood, M.N. 1978. Temperate-Zone Pomology. Freeman, New York, NY.

What we claim is:

1. A new and distinct variety of peach rootstock designated 'HBOK 50' as shown and described herein.

* * * * *

UNITED STATES PATENT AND TRADEMARK OFFICE

CERTIFICATE OF CORRECTION

PATENT NO. : PP22,208 P3
APPLICATION NO. : 12/653858
DATED : October 25, 2011
INVENTOR(S) : Fredrick A. Bliss et al.

It is certified that error appears in the above-identified patent and that said Letters Patent is hereby corrected as shown below:

On Title page, under "STATEMENT REGARDING FEDERALLY SPONSORED RESEARCH OR DEVELOPMENT", in column 1, line 8, delete "may have" and insert -- has --.

Signed and Sealed this
First Day of May, 2012

David J. Kappos

David J. Kappos
*Director of the United States Patent and Trademark Office*